(12) United States Patent
Thoma et al.

(10) Patent No.: US 11,224,669 B2
(45) Date of Patent: Jan. 18, 2022

(54) INACTIVATION OF PATHOGENS IN BIOLOGICAL MEDIA

(71) Applicant: FRAUNHOFER-GESELLSCHAFT ZUR FÖRDERUNG DER ANGEWANDTEN FORSCHUNG E.V., Munich (DE)

(72) Inventors: Martin Thoma, Leinfelden-Echterdingen (DE); Klaus Fischer, Grossbarthoff (DE); Javier Portillo, Dresden (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 185 days.

(21) Appl. No.: 16/329,373

(22) PCT Filed: Aug. 31, 2017

(86) PCT No.: PCT/EP2017/071879
§ 371 (c)(1),
(2) Date: Feb. 28, 2019

(87) PCT Pub. No.: WO2018/041953
PCT Pub. Date: Mar. 8, 2018

(65) Prior Publication Data
US 2019/0192704 A1   Jun. 27, 2019

(30) Foreign Application Priority Data

Sep. 1, 2016   (DE) ..................... 10 2016 216 573.9

(51) Int. Cl.
*A61L 2/00*   (2006.01)
*A61L 2/08*   (2006.01)
(Continued)

(52) U.S. Cl.
CPC ............. *A61L 2/007* (2013.01); *A61L 2/0029* (2013.01); *A61L 2/087* (2013.01); *A61L 2/26* (2013.01);
(Continued)

(58) Field of Classification Search
CPC .......... A61L 2/007; A61L 2/0029; A61L 2/26; A61L 2/087; A61L 2202/21; A61L 2202/11; A61L 2202/24
See application file for complete search history.

(56) References Cited

U.S. PATENT DOCUMENTS 1,068,898 A * 7/1913 Henri .................. A23L 3/28
                                                  250/433
3,926,556 A    12/1975 Boucher
(Continued)

FOREIGN PATENT DOCUMENTS

DE   2461783 A1   7/1976
DE   2721316 A1   11/1978
(Continued)

OTHER PUBLICATIONS

Guide to the nuclear wallchart (Year: 2000).*
(Continued)

*Primary Examiner* — Kevin Joyner
*Assistant Examiner* — Brendan A Hensel
(74) *Attorney, Agent, or Firm* — Harness, Dickey & Pierce, P.L.C.; Stephen T. Olson

(57) ABSTRACT

The invention relates to the processing of fluid biological media, especially of culture media or cell- or virus suspensions, potentially containing active pathogens, with the aim of inactivating these pathogens and/or modifying ingredients in these biological media by thermal or radiological treatment.

10 Claims, 8 Drawing Sheets

(51) Int. Cl.
*A61L 2/26* (2006.01)
*F04B 9/02* (2006.01)
(52) U.S. Cl.
CPC ............... *F04B 9/02* (2013.01); *F04B 9/025* (2013.01); *A61L 2202/11* (2013.01); *A61L 2202/24* (2013.01)

(56) References Cited

U.S. PATENT DOCUMENTS

| | | | | |
|---|---|---|---|---|
| 3,988,588 | A * | 10/1976 | Offermann | G21K 5/04 |
| | | | | 250/492.3 |
| 4,074,138 | A | 2/1978 | Bosshard | |
| 4,201,918 | A | 5/1980 | Latzer | |
| 6,596,230 | B1 * | 7/2003 | Woo | A61L 2/0011 |
| | | | | 250/433 |
| 6,643,538 | B1 * | 11/2003 | Majewski | A61B 1/042 |
| | | | | 348/162 |
| 6,719,125 | B1 * | 4/2004 | Hollander | B65G 1/06 |
| | | | | 198/781.02 |
| 6,756,597 | B2 * | 6/2004 | Avnery | A61L 2/08 |
| | | | | 210/386 |
| 10,080,795 | B2 | 9/2018 | Ulbert et al. | |
| 2009/0081340 | A1 | 3/2009 | Forney | |
| 2015/0343105 | A1 * | 12/2015 | Akahori | B08B 9/032 |
| | | | | 134/10 |
| 2015/0362243 | A1 | 12/2015 | Ko | |
| 2016/0158339 | A1 | 6/2016 | Ulbert et al. | |
| 2018/0353594 | A1 | 12/2018 | Ulbert et al. | |
| 2019/0175769 | A1 * | 6/2019 | Schonfelder | A61L 2/007 |

FOREIGN PATENT DOCUMENTS

| | | |
|---|---|---|
| DE | 19958021 A | 6/2000 |
| DE | 19901058 C2 | 4/2003 |
| DE | 102013012455 A1 | 2/2015 |
| FR | 2760445 A1 | 9/1998 |
| GB | 191012947 A | 4/1911 |
| GB | 2424877 A | 10/2006 |
| JP | 2005305331 A | 11/2005 |

OTHER PUBLICATIONS

International Search Report (in English and German) and Written Opinion (in German) issued in PCT/EP2017/071879, dated Nov. 24, 2017; ISA/EP.

International Search Report and Written Opinion translated to English issued in PCT/EP2017/071879, dated Mar. 14, 2019; ISA/EP.

* cited by examiner

INACTIVATION OF PATHOGENS IN BIOLOGICAL MEDIA

CROSS-REFERENCE TO RELATED APPLICATIONS

This application is a 371 U.S. National Stage of International Application No. PCT/EP2017/071879, filed Aug. 31, 2017, which claims priority to German Patent Application No. 10 2016 216 573.9, filed Sep. 1, 2016. The entire disclosures of the above applications are incorporated herein by reference.

FIELD

The invention relates to the processing of fluid biological media, especially of culture media or cell- or virus suspensions, potentially containing active pathogens, with the aim of inactivating these pathogens and/or modifying ingredients in these biological media by ionizing beta radiation.

BACKGROUND

As is known, pathogenic substances, including toxins or pathogens such as viruses, virus particles, bacteria or other organisms, can be inactivated by exposure to thermal or ionizing radiation—primarily UV, X-ray or gamma radiation, as well as beta radiation. The pathogens are modified in such a way that their pathogenic effect on an animal or human mechanism or a cell or tissue culture is minimized or completely eliminated. Such thermal or ionizing radiation—for example, with non-thermal electrons (beta radiation)—alters the structural integrity of one or more structural or functional components of these pathogens at the molecular level, thus leading to their inactivation. The problem with this is that, according to a dose/effect correlation, a radiation dose which is too low leads to incomplete or inadequate inactivation of the pathogens; whereas a radiation dose which is too high can cause undesirable structural changes and modifications in other components of the biological medium. This is particularly problematic in the manufacture of vaccines from suspensions of active pathogens—especially from virus suspensions. If, for example, virus suspensions are irradiated with low-energy beta radiation in order to deactivate the viruses, as described in DE 10 2013 012 455 A1, a radiation dose which is too low leads to undesired, incomplete inactivation of the viruses, whereas an excessive radiation dose leads to destruction or partial denaturating of the virus or viral antigen structures, and thus to an impairment of the immunogenic activity of the vaccine being produced. As such, with too low or too high a radiation dose, the virus suspension cannot be used as a vaccine.

However, irradiation with thermal or ionizing radiation can also be used for the targeted modification—that is to say, the conversion, mutagenesis, stimulation, transduction of cells or tissues—in cell research and in cell and tissue production, in particular also for fragmentating cellular DNA to prevent cell proliferation. In this case, control of the correct dose is highly important, especially if dose/effect dependencies of such radiation-induced modifications and effects on cells or tissues must first be determined scientifically.

In the context of the automation of biotechnological plants—in particular, plants for the production of vaccines, as well as plants for cell and tissue culturing—devices, methods, and means must be created which enable a particularly continuous processing of biological media—especially pathogenic suspensions, suspensions of cells or tissues, sterile media, etc. It is desirable in such cases to furnish methods and means for the dose-controlled irradiation of such biological media which are particularly fully automatic and continuously operable and which can be "inserted" into the ongoing flow of material in such plants. At the same time, it should be possible to clean, sterilize, or exchange such means as required in the plant. Likewise, the protection of personnel (from infection) and protection of products (from contamination) must be ensured.

SUMMARY

The invention was based on the technical problem of providing methods and means for automated, continuous irradiation of fluid biological media, particularly such as are suitable for subjecting a continuous fluid stream of the biological medium to a controllable radiation dose in an automatic line for the production or processing of such media. The invention must achieve an improved—that is, particularly, a dose-controlled—irradiation exposure, especially for the purpose of reliably inactivating pathogens or modifying biological media in a targeted manner according to the radiation. At the same time, an integral module should be furnished which is autonomously operable within the automatic line and is interchangeable and easy to clean, while also ensuring protection of personnel and protection of the product.

The technical problem is solved by a novel device for continuous homogenization of a fluid medium to expose the homogenized medium to beta radiation. According to the invention, a module is furnished for this purpose which enables the generation of a continuous fluid film of continuously supplied fluid, and which enables the irradiation of this fluid film, which has a predeterminable thickness—that is, surface/volume ratio. The module is designed according to the invention in the form of an exchangeable, integral cassette. The cassette is sterilizable—particularly, separately from the arrangement in which it can be utilized repeatedly for continuous, dose-controlled irradiation. The cassette according to the invention consists of a module housing, having a tub for receiving the continuously supplied fluid, and having a cylindrical roller which dips into this tub—particularly into the fluid supplied and received therein—and which can rotate in the same along an axis. In addition, the module has at least one inlet channel for supplying the fluid into the tub. There is at least one wiper lip, which is in intimate contact with the roller surface of the cylindrical roller—specifically, on the downward-rotating side of the roller in the direction of rotation of the roll—to wipe off the fluid film formed on the revolving roller surface of the fluid captured in the tub during the rotation of the roller. There is also an outlet channel for receiving and continuously discharging fluid which has been wiped off the roller surface by this wiper lip.

According to the invention, there is an overflow channel on the tub for draining excess supplied fluid from the tub, so as to define and maintain the level of fluid in the tub.

According to the invention, the cassette is further made of a housing cover which tightly seals the module housing to form the exchangeable cassette. The housing cover has at least one radiation-permeable window (radiation window) in the form of a metal window.

A preferred element of a first embodiment of the module housing of the cassette according to the invention is a special gap-forming element which is arranged on the side of the roller when the same runs into the fluid during rotation, at the position where the supplied fluid runs out of the tub onto the roller surface. The gap-forming element is distanced from the roller surface in such a manner that a capillary gap is formed at that position. This capillary gap extends at least to above the fluid level in the tub. According to the invention, this gap-forming element serves to generate and homogenize the fluid film formed on the roller surface.

The inventors have surprisingly found that the interaction of the elements according to the invention can generate a very continuous fluid film from a continuously supplied fluid, with a consistent thickness—and especially a consistent surface/volume ratio—during continuous operation. The fluid level in the tub, which is kept constant by the overflow channel included according to the invention in the tub of the module housing can, particularly in connection with the preferred specific gap-forming element which forms a capillary gap in cooperation with the roller surface, said capillary gap preferably extending to above this fluid level, result in a surprisingly uniform, continuous fluid film on the roller. In one of these preferred embodiments, the thickness of the fluid film can be adjusted within certain boundaries—specifically, via the width of the capillary gap and/or via the height of the portion of the capillary gap extending above the fluid level in the tub.

The type and quality of the fluid, its viscosity, and also the type and quality of the wetted surfaces—particularly, the surface of the roller—as well as the rotational speed of the roller also play a role in the formation of a suitable fluid film.

In an alternative embodiment of the module housing of the cassette according to the invention, such a special gap-forming element is omitted. This is especially because, in certain variants, even without such a specially shaped and arranged gap-forming element, it is possible to generate a continuous fluid film on the rotating roller in a sufficiently reliable manner.

In a preferred embodiment, the height of the at least one overflow channel in the tub, or the immersion depth, is variable, such that it is possible to set or predetermine the fluid level in the tub.

In a preferred embodiment, in addition to the overflow channel, there is at least one further means for fixing—that is, keeping constant—the fluid level in the tub of the module. The constant maintenance of the fluid level in the tub can preferably be improved by attaching a bubble detector or flow meter to the overflow channel, which detects the flow rate and/or gas bubbles which may arise. The type and quality of the flow at the overflow channel provides indirect information about the fluid level in the tub of the module. The sensor signal can be used to appropriately control the supply rate in the inlet channel. Bubble detection is mainly used for "function control". Continuous flow without bubbles at the overflow channel would suggest that the fluid in the inlet is in danger of running into the inactivated fluid reservoir, which should be prevented. In addition, the bubble detection during the start-up process can be used to check whether the cassette has been connected properly with proper tubing.

The pressure measurement is primarily used to check the tightness of the closed system before or during operation. The inside of the module is subjected to a slight overpressure or underpressure. If the module is leaking, this is indicated by a pressure change.

In a further alternative embodiment, the fluid supply to the roller is embodied as a so-called chambered doctor blade. The chamber is preferably sealed by sealing lips on the roller. Alternatively, the chamber forms a sealing capillary gap with the roller. The fluid is applied to the roller with regulated flow and/or pressure.

In all embodiments, the wiper lip is preferably oriented on the downward-rotating side of the roller against the downward-rotating direction of the rotating roller. It works like a scraper directed counter to the direction of rotation. Preferably, the wiper lip is pressed by the rotation onto the roller surface and contacts the same with no gap, and preferably over its entire width. Fluid wiped off the roller surface passes via the wiper lip preferably into an outlet groove or outlet channel arranged on the anchoring of the wiper to the module housing, and can be collected and discharged from the module housing.

In an alternative, preferred variant, the wiper lip is arranged on the downward-rotating side of the roller, in such a manner that it is oriented against the downward-rotating direction of the rotating roller. It forms, together with the surface of the roller, a transverse groove in which the fluid which is wiped off can collect. From there, it can flow over passively and be collected in a discharge groove arranged on the anchoring of the wiper, and be discharged from the module housing. Alternatively and preferably, however, the outlet channel at this position is embodied as at least one tube projecting into the groove formed between the wiper lip and the downward-rotating side of the roller. The fluid which is wiped off can preferably actively drain from the groove via this tube—particularly preferably by suction applied by means of a vacuum pump—and preferably a peristaltic pump—or alternatively by expulsion via overpressure. However, this particularly requires a reservoir with pressure compensation.

In a further alternative embodiment, the discharge of fluid from the roller surface is facilitated via a double wiper lip. At least the trailing (lower) wiper lip contacts the roller and is oriented counter to the downward-rotating direction of the rotating roller. The two wiper lips, running in parallel, form a chamber together with the roller surface in the manner of a chambered doctor blade. The chamber forms the outlet channel.

In a preferred embodiment, at least one wiper, which is set at a distance from the roller surface, is additionally arranged on the upward-rotating side of the roller, and accordingly downstream of the capillary gap which is established. The wiper serves to additionally homogenize the fluid film, and to set the film height for particularly viscous media. In a preferred variant of this embodiment, the distance of the wiper from the roller surface is adjustable, or the wiper can be swapped out for accordingly differently-sized wipers in the module so as to regulate the effect on the homogenization of the fluid film, and on the thickness of the fluid film, and as required. In a special variant of this embodiment, the wiper edge of the wiper has an arcuate or elliptical shape in order to homogenize the fluid film between the central section and the peripheral sections of the roller.

Preferred materials of the roller surface are selected from among: materials which reflect electrons and/or heat rays—particularly preferably from among metals of subgroup VIII (old IUPAC), and more preferably from among the metals platinum (Pt), gold (Au), chromium (Cr), nickel (Ni) and iron (Fe), and alloyed ferrous steels, especially chromium-nickel steel and other stainless steels. Particularly preferred is a gold (Au) coating; alternatively a platinum (Pt) coating is preferred. Alternatively or additionally, the roller surface is hydrophilized by means of chemical or plasma processes, which are known per se, in order to improve the formation of a closed fluid film on the surface. Alternatively or additionally, the surface of the roller is structured.

In a preferred embodiment, the surface of the roller is temperature-controlled by suitable measures—that is, in particular, cooled—to compensate for radiation-induced heating, specifically to prevent unwanted adverse radiation effects. In an alternative variant, the roller surface can be heated, particularly in order to enhance the radiation effect in conjunction with the thermal action, or to direct it specifically to thermally sensitive structures in the fluid medium. Particularly for this purpose, there is an additional circulation for conveying a cooling or heating fluid through the module, and particularly the roller. In an alternative embodiment, the temperature of the roller surface is only controlled by heat conduction via the module, which is temperature-controlled as a whole from the outside. In an alternative embodiment, the supplied medium which will be irradiated is tempered, preferably before it enters the module—and alternatively or additionally during the irradiation.

According to the invention, at least one radiation window is included on the housing cover of the cassette in order to seal the module housing in a gas-tight and airtight manner. In a preferred embodiment, to protect the radiation source, a radiation window is also included on the arrangement to which the cassette can be coupled. The type and design of the radiation window depends on the type and quality of the radiation. For irradiation with ionizing, short-wave radiation, UV-C or soft X-rays, radiation windows made of plastic or quartz glass can be used. However, according to the invention, metal windows are used for irradiation with X-ray radiation or beta radiation. Metals for the radiation windows are preferably selected from among titanium, magnesium and aluminum, and alloys thereof.

Preferably, the module housing is cooled before or during operation—for example, tempered to 4° C. In this case, fluid can condense on the radiation window if there is ambient humidity. For this reason, in a preferred embodiment, the radiation window can be washed with dry gas to prevent condensation from forming on it. Preferably, the dry gas simultaneously serves to cool the radiation window during the irradiation.

In a particular variant, the rotation of the roller in the module is generated via the pressure and flow of the fluid supplied to the module for the purpose of irradiation. In a first variant, the fluid which is supplied via the at least one inlet channel drives the rotation of the roller in the primary fluid stream. That is, all of the supplied fluid, which is "converted" to a continuous fluid film, serves to drive the roller. In a preferred embodiment of this variant, a turbine element or vaned wheel element is arranged on the roller axle or in the roller, and all of the supplied fluid flows through the same. In a further such variant, the roller surface is designed to be "adhesive" for the supplied fluid, in such a manner that the fluid flowing over the gap-forming element onto the roller surface generates movement in the roller with friction, due to the prevailing pressure and gravity conditions.

In an alternative variant, a partial stream of the supplied fluid drives the roller. In this case, a portion of the supplied fluid is "converted" into the continuous fluid film, and another portion serves to drive the roller and flows back into the tub. In this variant, a peripheral paddle wheel structure is preferably provided at one or more positions along the outer surface of the roller. A partial stream of the supplied fluid is directed to it and thereby causes the roller to rotate. In this case, this portion of the supplied fluid particularly does not form a continuous fluid film, and is not wiped by the wiping edge on the downward-rotating side of the roller and discharged via the outlet channel of the module. For this purpose, the wiper edge at the position of the rotating paddles has a recess which prevents fluid at this position from being wiped off.

In alternative or additional embodiments, the roller of the module can be made to rotate by an external drive. In a simple embodiment, the axle shaft of the roller of the module is routed for this purpose out of the module housing to the outside, where it can engage via a suitable mechanical coupling with an external drive, such as a geared motor or step motor. In one embodiment, the roller axis is directly routed on the module housing to the outside. In an alternative embodiment, the drive shaft which leads out of the module housing is coupled to the roller axle shaft inside the module housing via a transmission—preferably a spindle gear, gears or toothed belts.

The shaft feedthrough of the drive shaft or roller axle is preferably designed as a double shaft seal in the module housing, preferably with a flushable internal space. The internal space can be rinsed with aseptic and/or disinfecting rinsing medium.

In an alternative and preferred embodiment, the torque coupling between the roller and the external drive element is a contactless magnetic coupling—particularly via magnetic elements inserted into the roller, which form a magnetic coupling together with a corresponding structure on the drive element. In a preferred embodiment of this variant, the magnetic elements of the roller can be brought into contact with an external electromagnetic drive—particularly a stationary magnetic coil arrangement which is energized with alternating current—thereby together forming an electric motor as a whole.

The interchangeable cassette according to the invention can be used in a fixed apparatus—for example, within automatic lines—and can be exchanged as needed for the purpose of cleaning or sterilization. It is envisaged that the cassette comprises all the connections for the supply and discharge of the biological fluid in this case. These can be configured with quick-change adapters. In a preferred embodiment, the quick-change connections for the fluid inlets and outlets are arranged on the module housing in such a way that the fluid connections are established automatically upon the insertion or plugging of the cassette into the sterilization arrangement. Such connections can be CIP ("clean in place"), WIP ("wash in place") or SIP ("sterilization in place") connections. Alternative connections known per se include valves and sterile connectors such as Luer-Lock and related systems.

The interchangeable cassette according to the invention itself preferably has a modular structure, such that elements within the module which determine the formation, and particularly the thickness, of the desired fluid film can be exchanged individually. For example, a plurality of differently sized gap-forming elements can be furnished; these can be exchanged in the module, in the manner of a modular system, to adjust the thickness of the fluid film. Likewise, the roller itself can be provided in different variants, the variants differing substantially in the type and properties of the roller surface. Due to the modular structure, particularly the design of the module as an interchangeable and closed cassette, it is possible to operate a complete system for the inactivation of dangerous pathogens even in lower-security laboratories and automated lines. Due to the optional, fully enclosed design, it is possible to configure and prepare the module as a whole, including the necessary fluid inlets and outlets and the associated reservoirs in a first high-security laboratory, and to then move this arrangement in a sterile, closed configuration into the lower-security automatic line, where the radiation treatment can be performed to inactivate the pathogenic agents. The fully closed design of the module can prevent contamination of the other automatic parts, particularly the radiation source, the drives of the roller, and the pumps. At the same time, this results in, or improves, protection for personnel and the product.

In a first variant, the module is open on one side and allows free projection of the thermal or ionizing radiation onto the fluid film exposed on the roller surface. In this case, this module is preferably inserted or plugged or otherwise coupled into a fixed arrangement for operation, and is sealed to the same. This fixed arrangement in turn contains at least the radiation source, and preferably additionally contains means for transporting the fluid through the module, and/or additionally contains means for driving the rotation of the roller in the module.

In an alternative embodiment, the module is fully self-contained and is preferably provided as an exchangeable, standardized cassette. There is preferably a sealed housing cover for sealing the module housing, wherein the housing cover particularly has a gas-tight and fluid-tight, but radiation-transparent radiation window for the purpose of irradiation, through the window, of the fluid film formed on the roller surface by means of an external radiation source.

The invention also relates to a device for the continuous, dose-controlled irradiation of fluid, particularly of a biological medium, for example for inactivating pathogens in the medium or for modifying components of the medium by means of ionizing or thermal radiation, which contains the module according to the invention and additionally at least one radiation source, wherein the module can particularly be coupled directly to the radiation source. Furthermore, the device has at least one or more pumps for the continuous active transport of this fluid through the module.

In a variant, there is additionally at least one reservoir containing the fluid to be irradiated, and at least one collecting vessel for receiving the irradiated fluid which flows out of the module. In a preferred embodiment, the purpose of the reservoir is to continuously supply the module with this fluid through the inlet, via a first supply line. The overflow of the module preferably opens into the reservoir. The fluid is actively transported into the module, particularly by the reservoir being pressurized—especially if the overflow does not return to the reservoir—and/or by pump elements in the inlet. The fluid is passively transported from the overflow of the module into the reservoir—particularly facilitated by the negative pressure generated in the reservoir which arises when the supply fluid is suctioned out of the reservoir, and/or gravity-assisted. Alternatively and preferably, the fluid is actively transported via a pump—particularly a peristaltic pump.

The collecting vessel for receiving the irradiated fluid is connected to the outlet channel of the module. In a preferred embodiment, a pressure compensating venting channel is additionally included, and connects the outlet side of the module with the outlet vessel. The wiped, irradiated fluid is preferably transported away passively—particularly gravity-assisted—or alternatively by active transport, by the application of pressure or vacuum to the outlet vessel, and/or by active pumping elements in the outlet branch of the module.

Preferably, this device additionally contains at least one mechanical or electromagnetic drive element—optionally with suitable mechanical or contactless coupling elements for driving the rotations of the roller in the module.

The module according to the invention and the device according to the invention are specifically suitable for homogenizing continuously supplied fluid for the purpose of dose-controlled irradiation of the fluid. This primarily functions, as described herein, to bring about the targeted inactivation of pathogens in the fluid. Accordingly, a further object of the invention is a method for inactivating pathogens in a biological fluid—which is particularly carried out continuously. The method according to the invention comprises at least the following steps: In step (a) the fluid, which potentially contains active pathogens, is supplied, particularly actively, to the module according to the invention. In step (b), the roller is rotated in the module according to the invention, such that a continuous fluid film of a predeterminable thickness is formed from the supplied biological fluid on the revolving roller surface. In step (c), the fluid film formed and exposed on the roller surface is irradiated with a pathogen-inactivating dose of ionizing radiation, the radiation dose being determined by the radiation intensity of the radiation source passing through the radiation-exposed volume of the fluid, which is determined by the radiation window and the thickness of the fluid film which forms—and also preferably by the flow velocity or flow rate of the fluid film, which can be determined by the rotation speed of the roller. In step (d), the fluid irradiated after passing through the radiation window and wiped off the roller surface is discharged from the module and collected. This fluid contains pathogens which are inactivated in a dose-dependent manner.

A method according to the invention also generally relates to the thermal or ionizing irradiation of a fluid by means of the module according to the invention, comprising the steps of (a): supplying the fluid to the module, (b) rotating the roller in the module such that a continuous fluid film of determinable thickness forms on the revolving roller surface, (c) irradiating the fluid film on the roller surface with thermal or ionizing radiation; and (d) collecting the irradiated fluid which can be discharged from the module.

Preferably, the radiation dose is determined by the radiation source and the rotational speed. Since a dose gradient arises within the fluid, it is particularly desirable in many cases for the layer of the fluid film on the roll to have the least possible height. This advantageously results in minimal differences in the radiation dose within the transported fluid. It may be desired to set the layer height (greater than the least possible height) in instances where higher throughput is desired—in the event that the dose gradient in the fluid is acceptable. In this case, the thickness of the fluid film is preferably regulated by adjusting the capillary gap on the outlet element of the module—optionally in cooperation with an additionally-included wiping element. Alternatively, or preferably additionally, the dose is determined and regulated by the rotation speed of the roller, wherein the rotation speed decisively determines the residence time of a specific volume of the medium in the irradiated area. The rotational speed also optionally determines the thickness of the fluid film. In addition, the dose and penetration depth can be determined by direct control of the radiation source—for example the beta radiation source—in a manner which is known per se.

A further object of the invention is the use of the module or device of this invention for the continuous inactivation of pathogens in a fluid biological medium, preferably a virus suspension, by means of ionizing radiation.

Finally, a further object of the invention is the use of the module or device of this invention for modifying biological media by means of ionizing radiation.

DRAWINGS

The drawings described herein are for illustrative purposes only of selected embodiments and not all possible implementations, and are not intended to limit the scope of the present disclosure.

Corresponding reference numerals indicate corresponding parts throughout several of the drawings.

DETAILED DESCRIPTION

The invention is explained in more detail by the following figures and embodiments.

Figure 1:
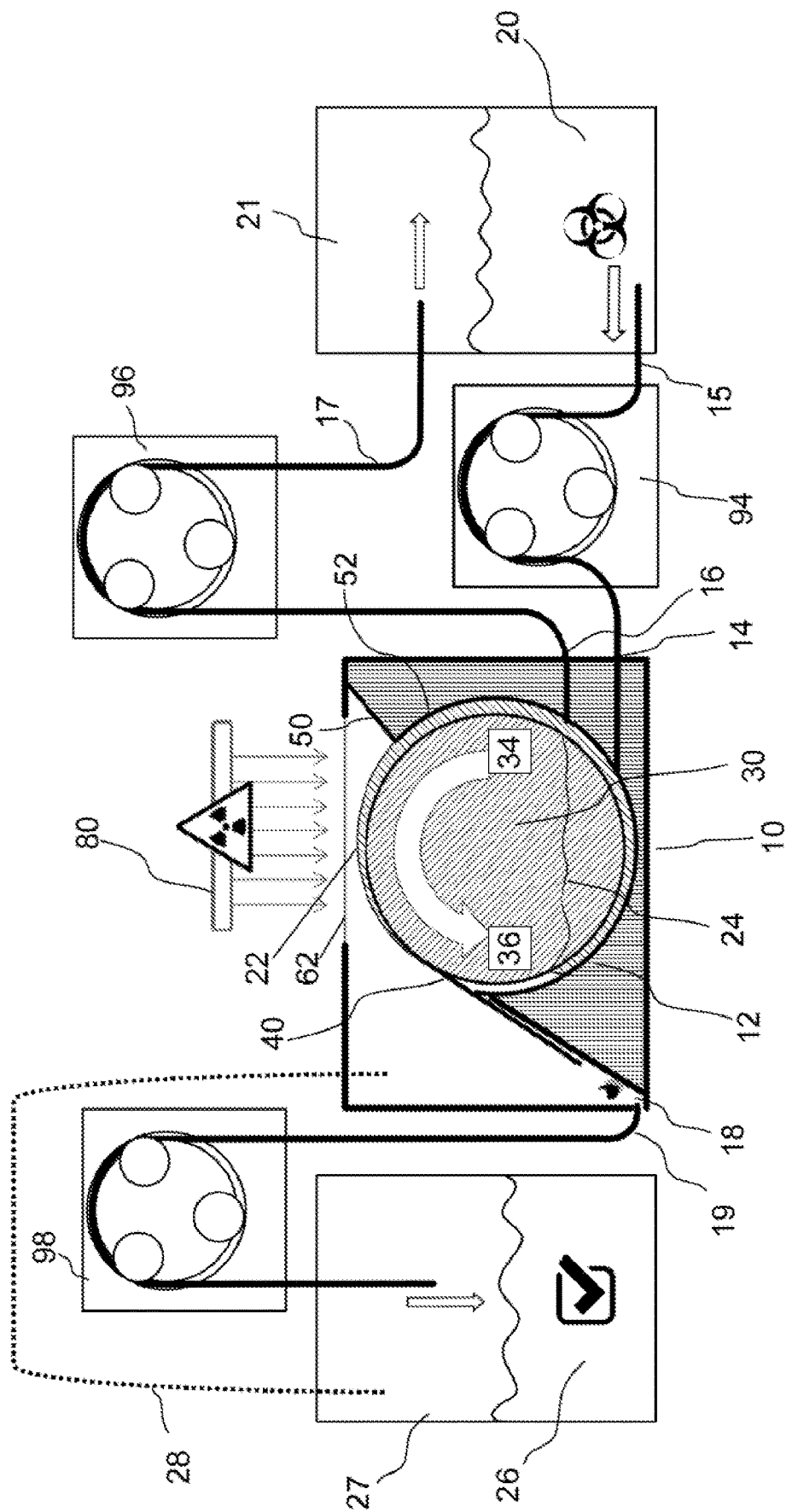
FIG. 1 is a schematic illustration show the the overall structure for continuous irridation of pathogen-containing fluids, for the purpose of inactivating the pathogens, using the module according to the invention.

FIG. 1 schematically shows the overall structure for continuous irradiation of pathogen-containing fluids, for the purpose of inactivating the pathogens, using the module according to the invention. A fluid medium 20 which potentially contains pathogens has been furnished in a reservoir 21. The fluid is actively conveyed into the tub 12 via the supply line 15 and the peristaltic pump 94 via the inlet 14 on the module housing 10. An overflow 16 included in the module housing returns excess fluid into the reservoir 21 via line 17, and an optional peristaltic pump 96. The fluid level 24 in the tub 12 is kept constant. The cylindrical roller 30 rotates in the fluid 20 in the tub 12. The gap-forming element 50 arranged according to the invention on the upward-rotating side 34 of the roller forms a capillary gap 52 from the roller surface—the capillary gap 52 also extending above the fluid level 24. Upon rotation of the roller 30, the capillary gap 52 facilitates the formation and homogenization of a fluid film 22 on the roller surface. The fluid film 22 which is formed is guided past a radiation window 62 and is exposed at that point to the radiation of a radiation source 80. After the irradiation on the upward-rotating side 36 of the roller 30, the fluid film 22 is substantially completely removed or wiped off by a wiping edge 40, which contacts and seals against the roller surface at that position. The removed, irradiated fluid 26 is collected and removed into a collecting vessel 27 via the outlet channel 18 via line 19—optionally via peristaltic pump 98. An optional pressure line 28 provides pressure equalization.

Figure 2:
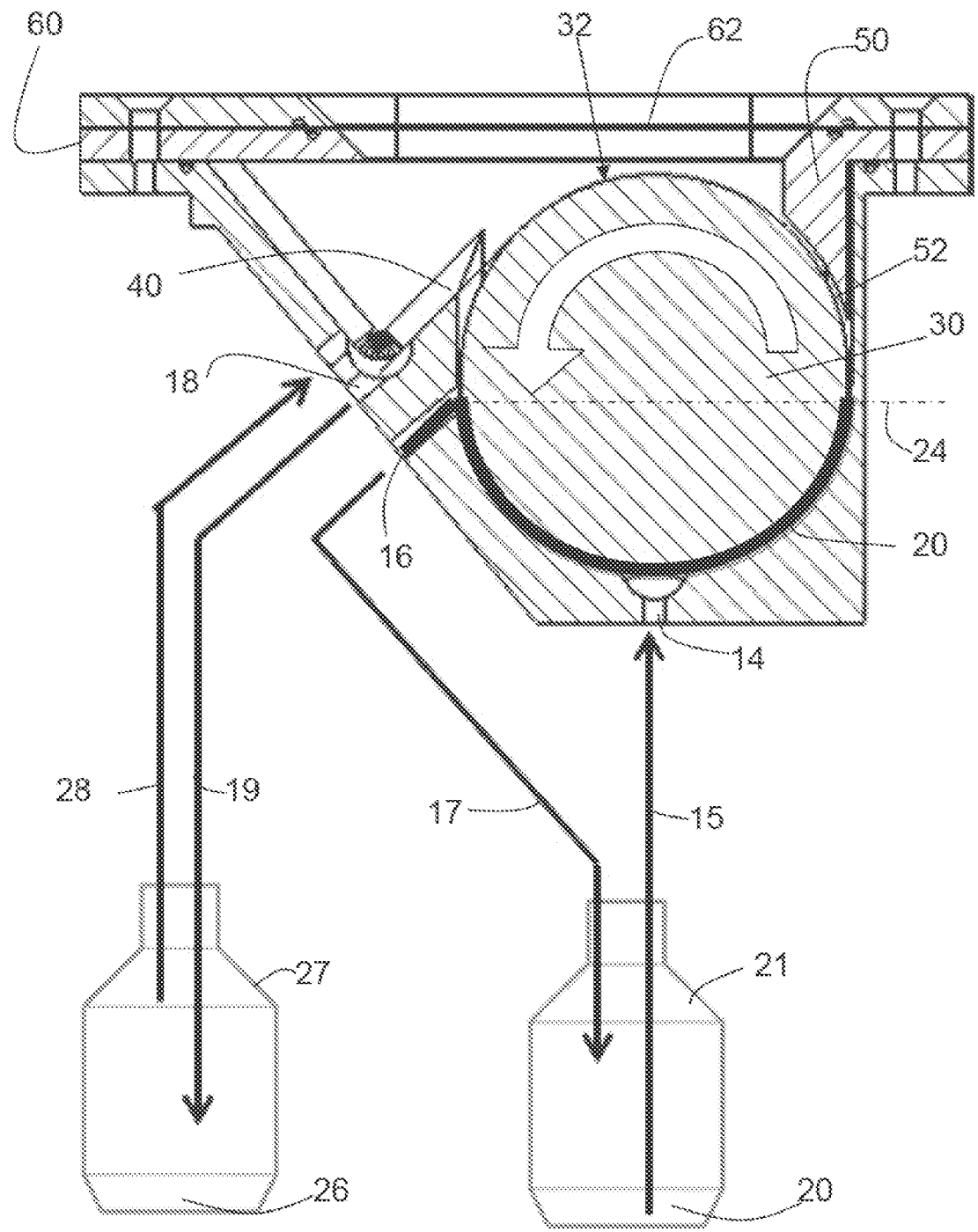
FIG. 2 is a schematic illustration of a specific embodiment according to invention showing principle routing of the fluid flow in the overall arrangement analogous to FIG. 1.

FIG. 2 shows the principle routing of the fluid flow in the overall arrangement analogous to FIG. 1, on the basis of the schematic sectional drawing of a specific embodiment of the module according to the invention.

Figure 3:
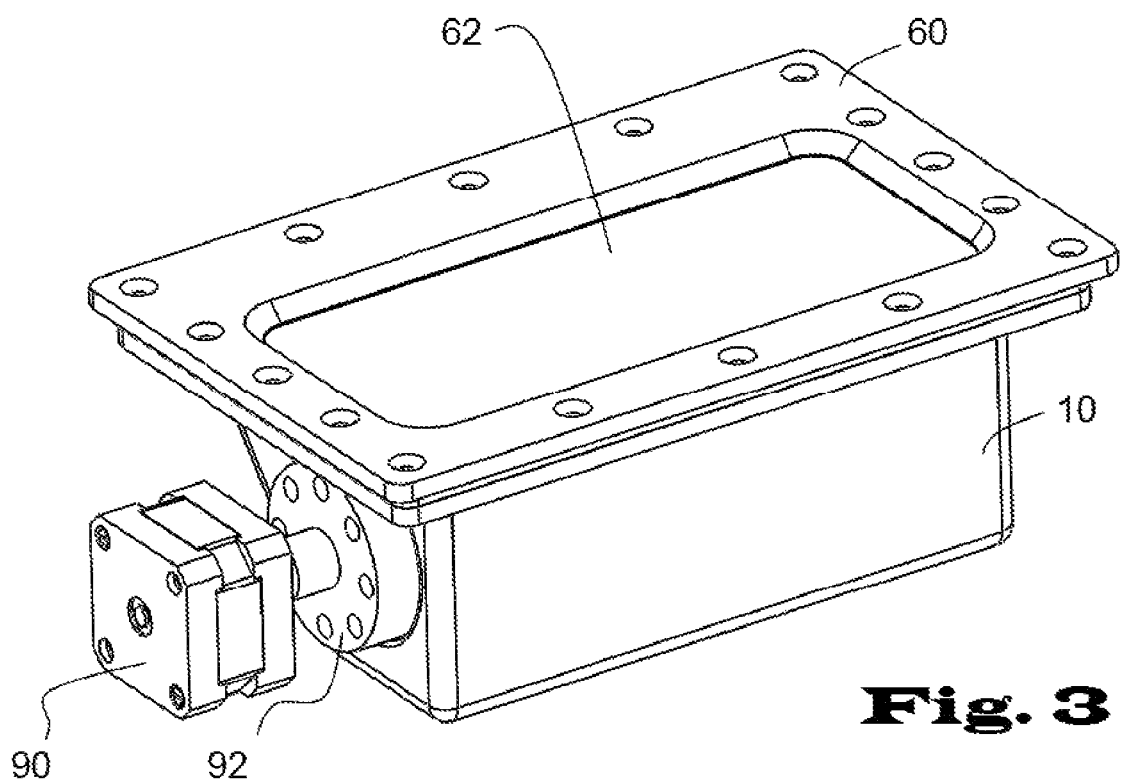
FIG. 3 shows a perspective, plan view of a specific embodiment of the module according to the invention.

FIG. 3 shows a perspective, plan view of a specific embodiment of the module 10 according to the invention, with the tightly-fitted cover 60 with the radiation window 62. A drive element 90 with a coupling element 92 is shown on the module, for driving the roller contained in the module. The roller is driven in the module 10 in this case without contact, via magnetic elements in the coupling element 92 and corresponding magnetic elements in the roller.

Figure 4:
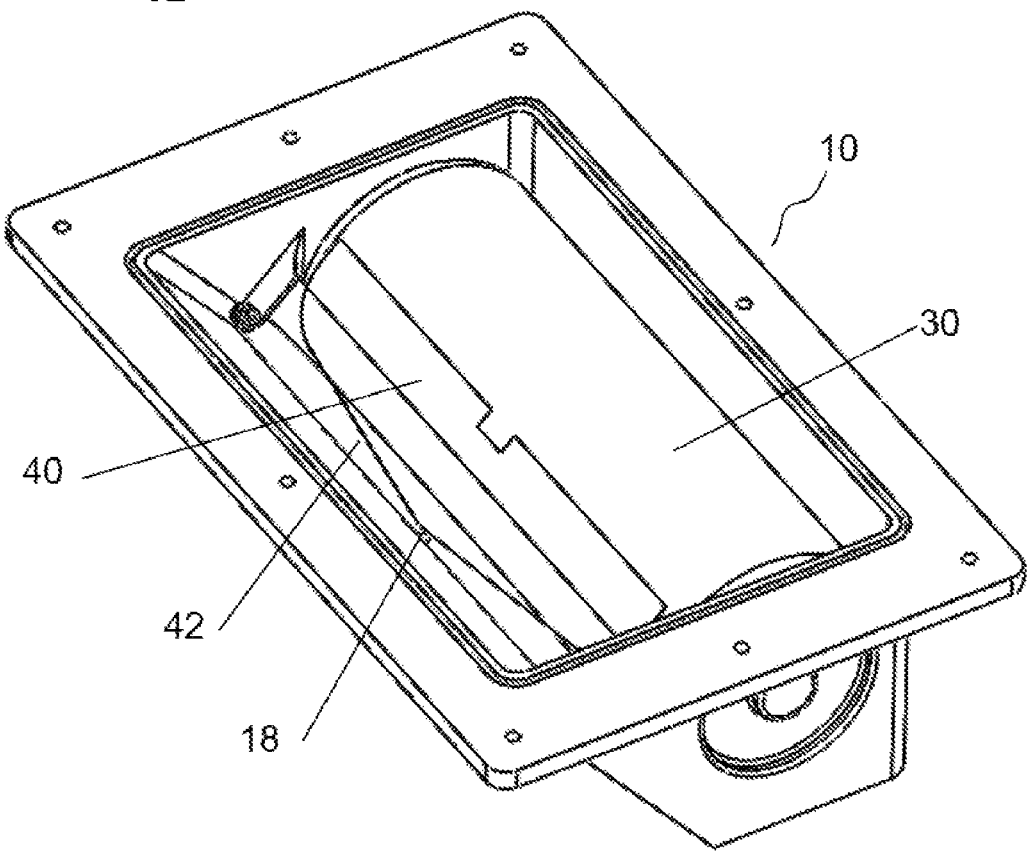
FIG. 4 is a perspective view of the module 10 according to FIG. 3 with the cover removed.

FIG. 4 shows a perspective view of the module 10 according to FIG. 3, with the cover removed, and with a view of the rotatable cylindrical roller 30, the wiping edge 40 in contact with the surface of the cylindrical roller 30—in this case in the form of a wiping plate compelled by spring force, and a collecting channel 42 which opens into the outlet channel 18.

Figure 5:
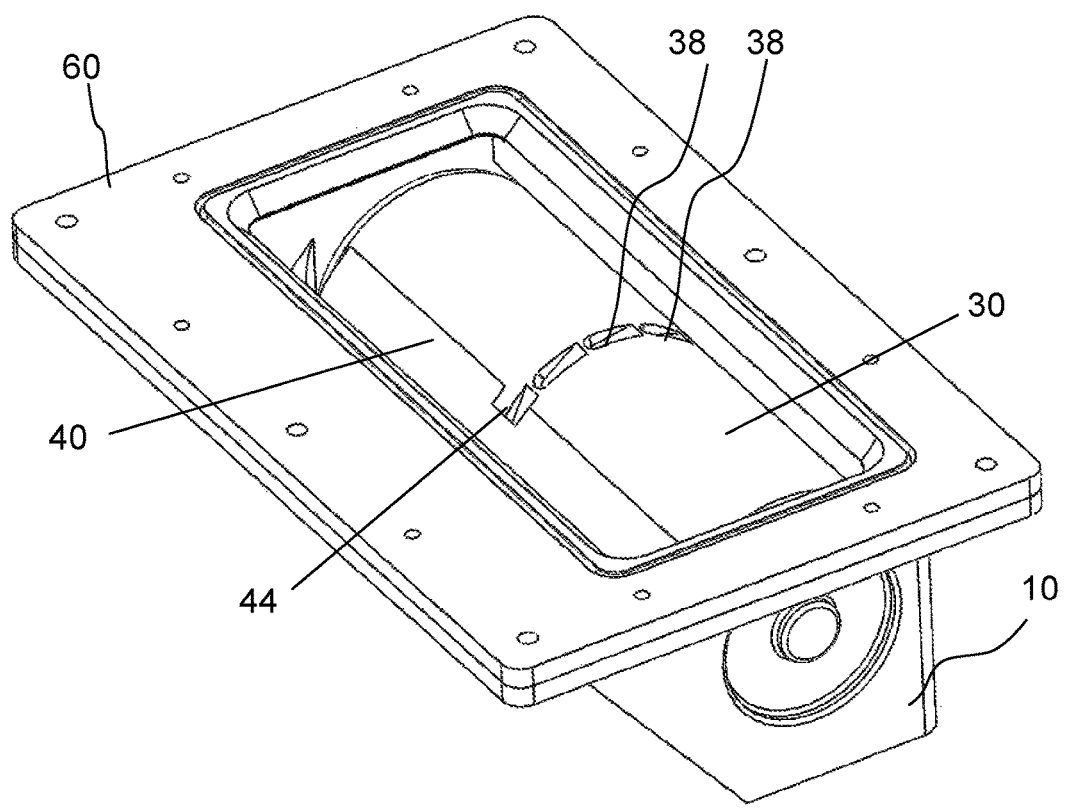
FIG. 5 is an alternative embodiment of a module 10 according to the invention.

FIG. 5 shows an alternative embodiment of a module 10 according to the invention, with the cover 60 which in this case has an optically transparent radiation window. The cylindrical roller 30 rotatable in the tub of the module housing has at least one revolving paddle wheel ring with paddle elements 38 which are filled with fluid supplied by the module in order to cause the roller 30 to rotate. In this specific embodiment, the wiping edge 40 has a recess 44 at the position of the revolving paddle elements 38 in order to not wipe off fluid circulating at this position, which does not form a defined fluid film.

Figure 6:
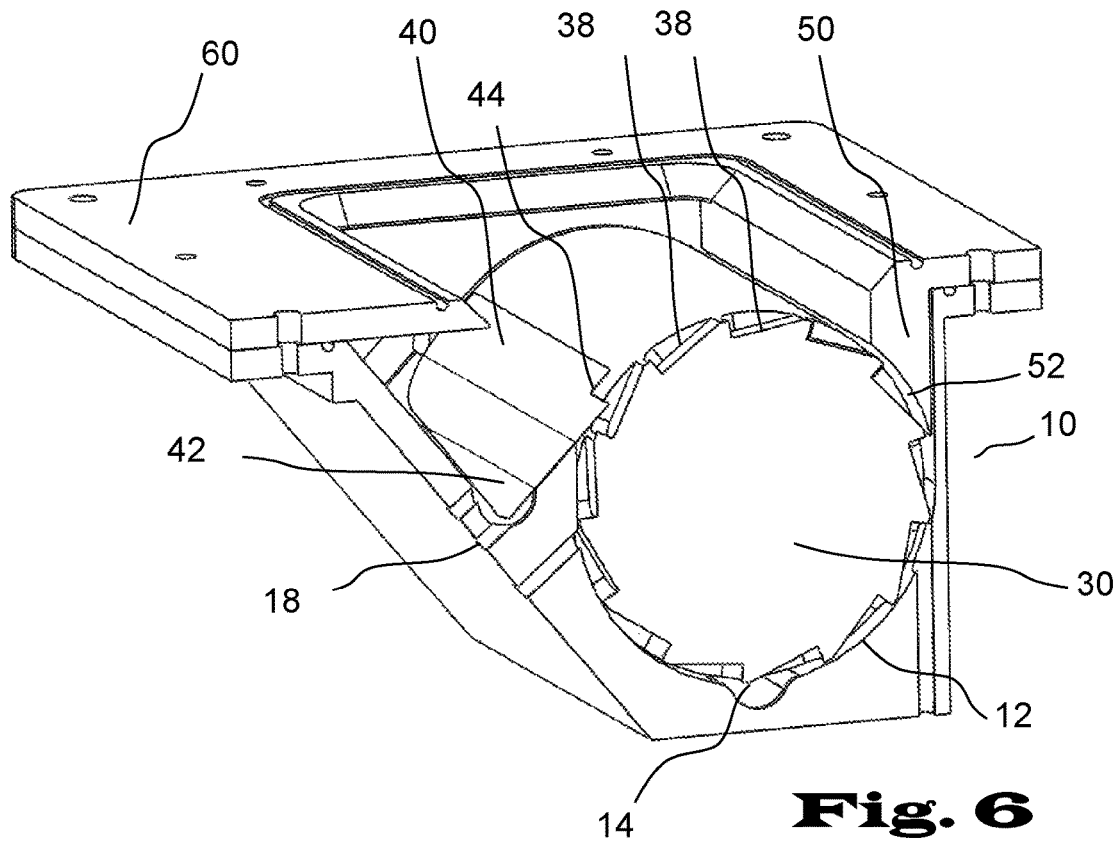
FIG. 6 is a cutaway view of the specific embodiment of FIG. 5.

FIG. 6 shows a cutaway view of the specific embodiment of FIG. 5. An inlet channel 14 and an overflow channel 16 are formed on the tub 12 in which the cylindrical roller 30 rotates. In the illustrated specific embodiment, the gap-forming element 50 is preferably constructed as a single piece together with the cover 60 which can be placed on the module housing, to form the capillary gap 52. On the downward-rotating side of the roller 30, the wiping edge 40 is designed with a recess 44 in the form of a wiping plate compelled against the roller surface by spring force. The fluid wiped off the roller surface is collected in the collecting channel 42 and discharged from the module via the outlet channel 18.

Figure 7A:
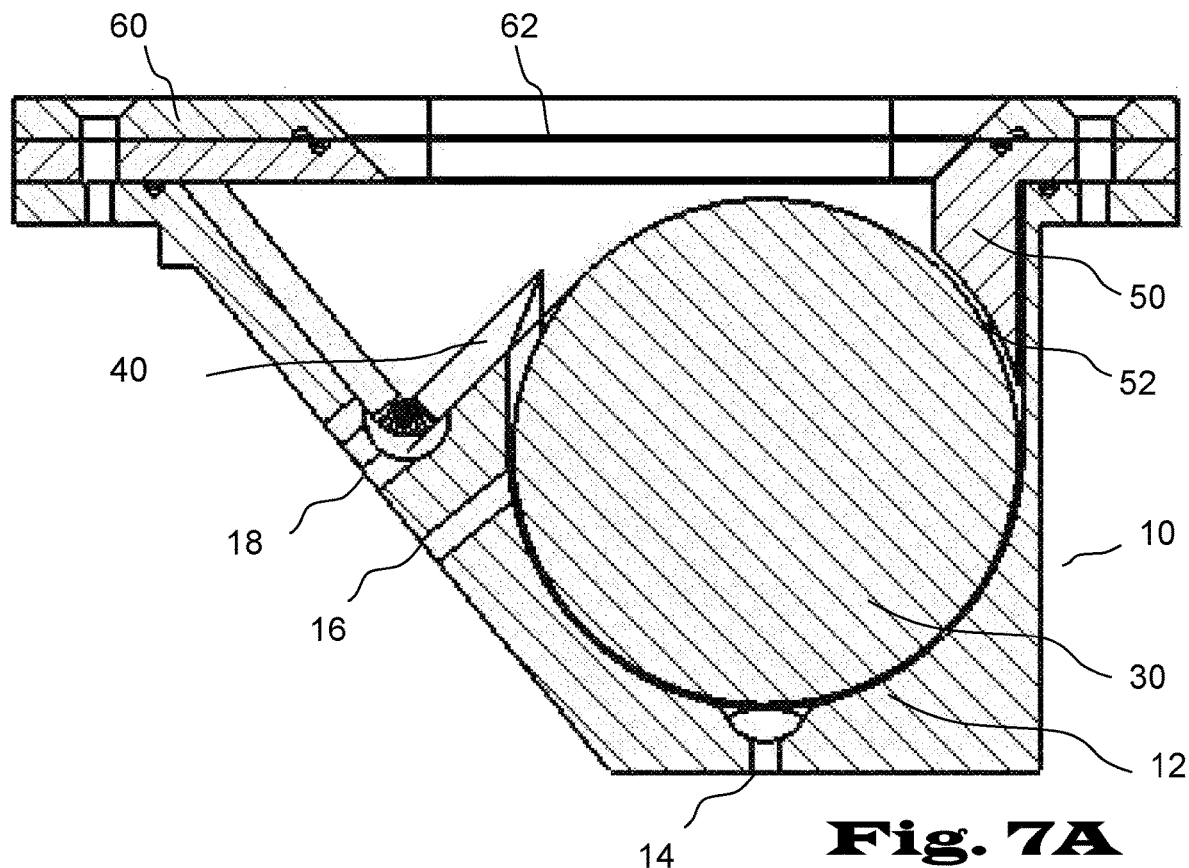
FIGS. 7A and 7B are schematic sectional views of a specific embodiment of the middle of module 10 according to FIG. 2.
Figure 7B:
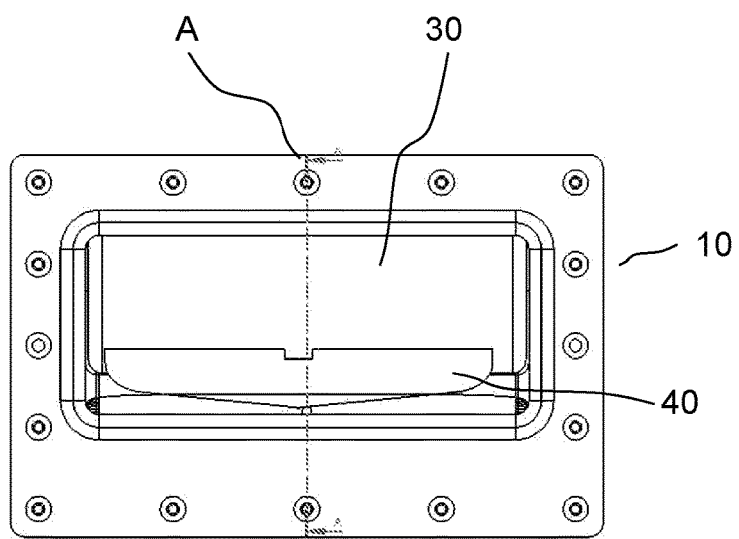

FIGS. 7A and 7B are schematic sectional views of a specific embodiment of the module 10 according to FIG. 2. FIG. 7B shows a plan view of the same module as a whole with a section line A included. This designates the sectional plane in the corresponding FIGS. 7A, 6 and 2.

Figure 8A:
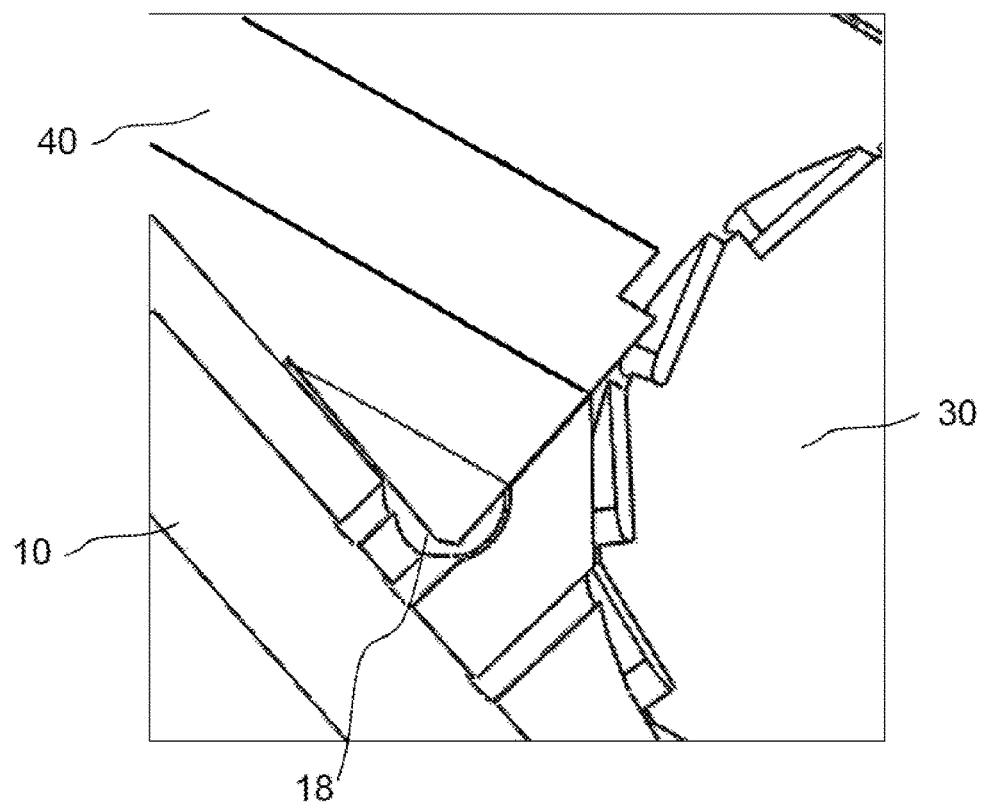
FIGS. 8A and 8B are schematic sectional views of the embodiments shown in FIGS. 4 and 5 and/or 9 and 10A and 10B.
Figure 8B:
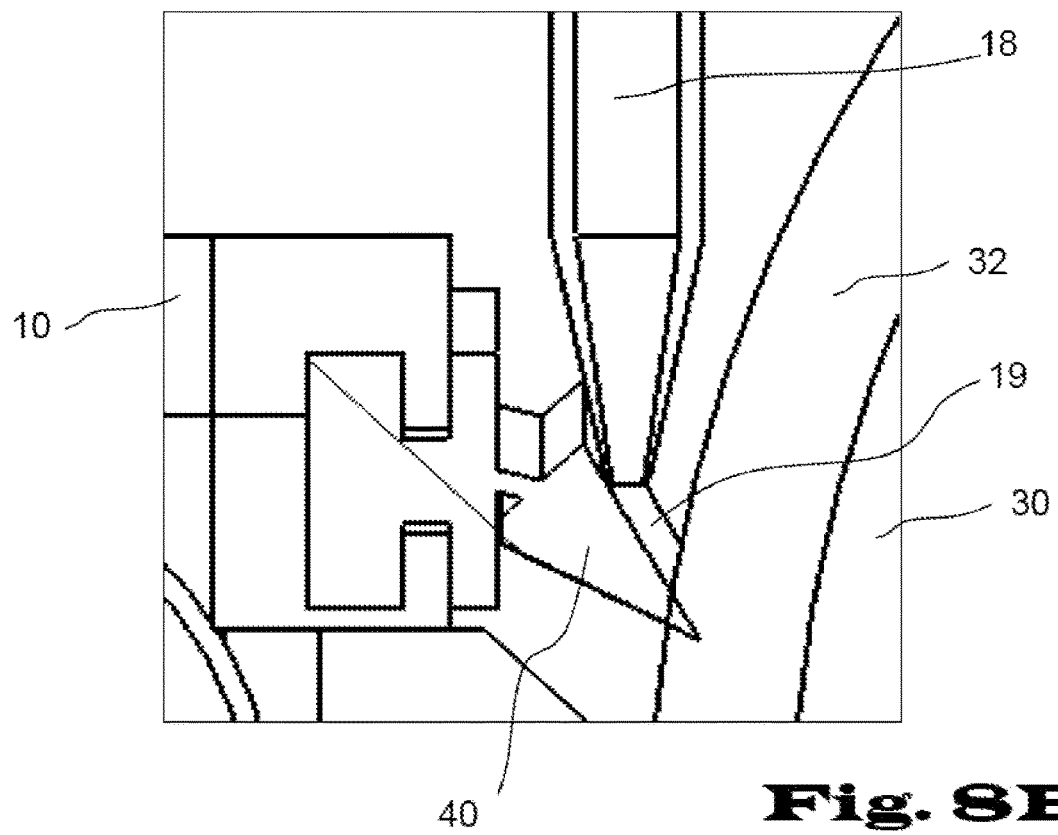

FIGS. 8A and 8B are schematic sectional views of portions of the embodiments shown in FIGS. 4 and 5 and/or 9 and 10A and 10B. FIG. 8A shows a first embodiment and arrangement of the wiping edge 40 on the roller 30. The wiper 40 is oriented counter to the direction of rotation of the roller 30. FIG. 8B shows an embodiment and arrangement of the wiping edge 40 as an alternative. The wiper 40 designed as a wiper lip is oriented in the direction of rotation of the roller 30. In the case of the embodiment according to FIG. 8A, the fluid wiped off the roller 30 with the wiper 40 can flow past the wiper into the outlet 18 designed as a groove. In the case of the embodiment according to FIG. 8B, the fluid wiped off by the roller 30 with the wiper lip 40 can flow into a groove 19 formed between the roller surface and the wiper lip 40 and can be actively or passively removed therefrom via the outlet 18 designed as a cannula.

Figure 9:
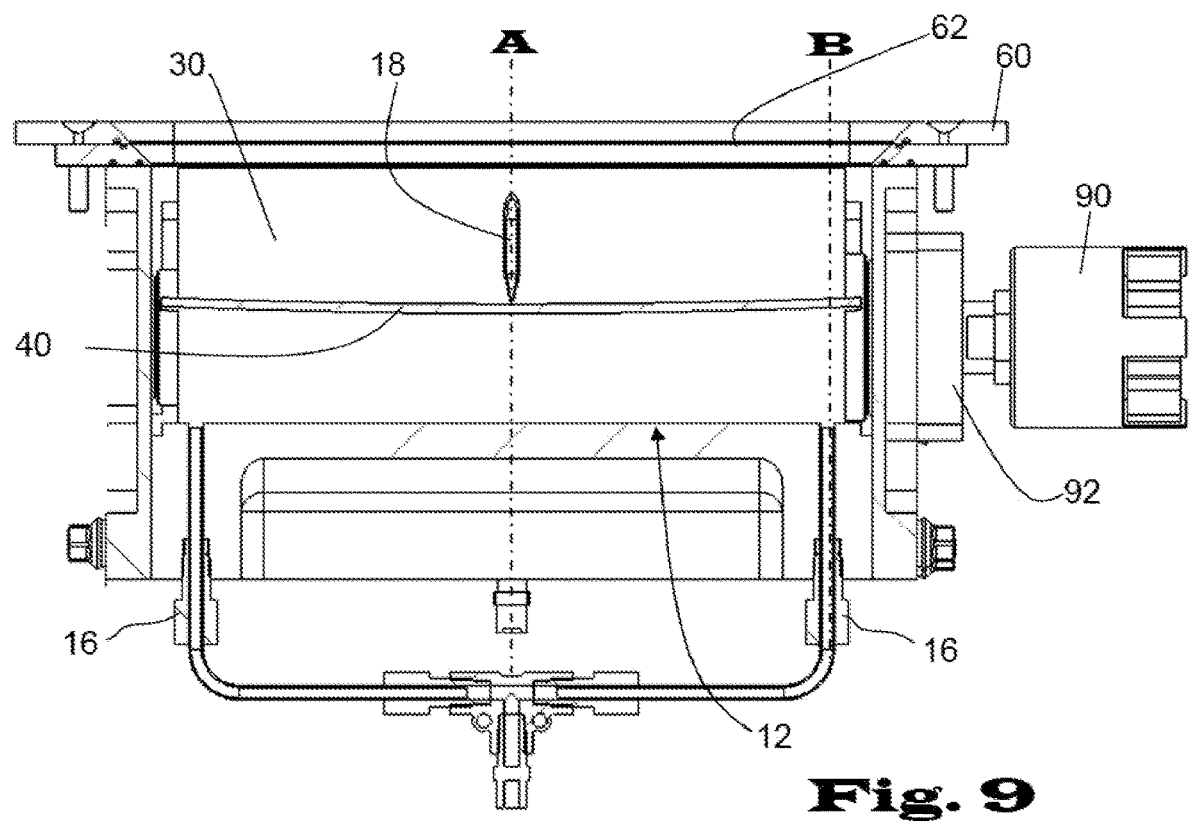
FIG. 9 is a schematic cross-sectional sectional view of a further embodiment of a casette of the invention.

FIG. 9 shows a schematic cross-sectional view of a further embodiment of the cassette. The sectional plane of the view is located in the region of the wiper lip 40. The module housing 10 is closed by the housing cover 60. The radiation window 62 is situated in the housing cover 60. The wiper lip 40 in front of the roller 30 in a preferred embodiment according to the invention has an arcuate form, such that fluid wiped off of the roller 30 primarily collects, due to gravity, in the region of the outlet tube 18, which is preferably arranged centrally. In the illustrated embodiment, the rotation of the roller is facilitated via an axially-disposed coupling 92, comprising the shaft passing through the housing 10, and the drive unit 90. In the illustrated embodiment, the immersion depth of the overflow tubes 16 which project into the tub 12 can preferably and optionally be adjustable, such that the fluid level in the tub 12 can be preset.

Figure 10A:
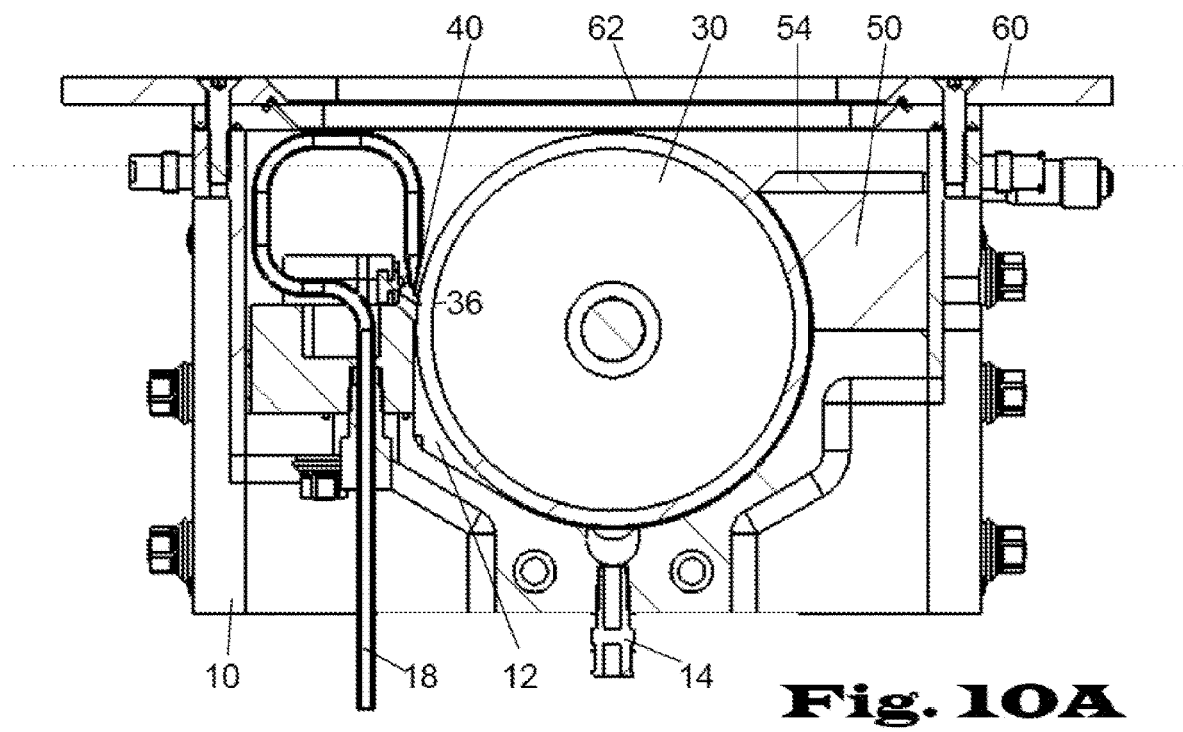
FIGS. 10A and 10B are schematic sectional views of embodiment of FIGS. 9.
Figure 10B:
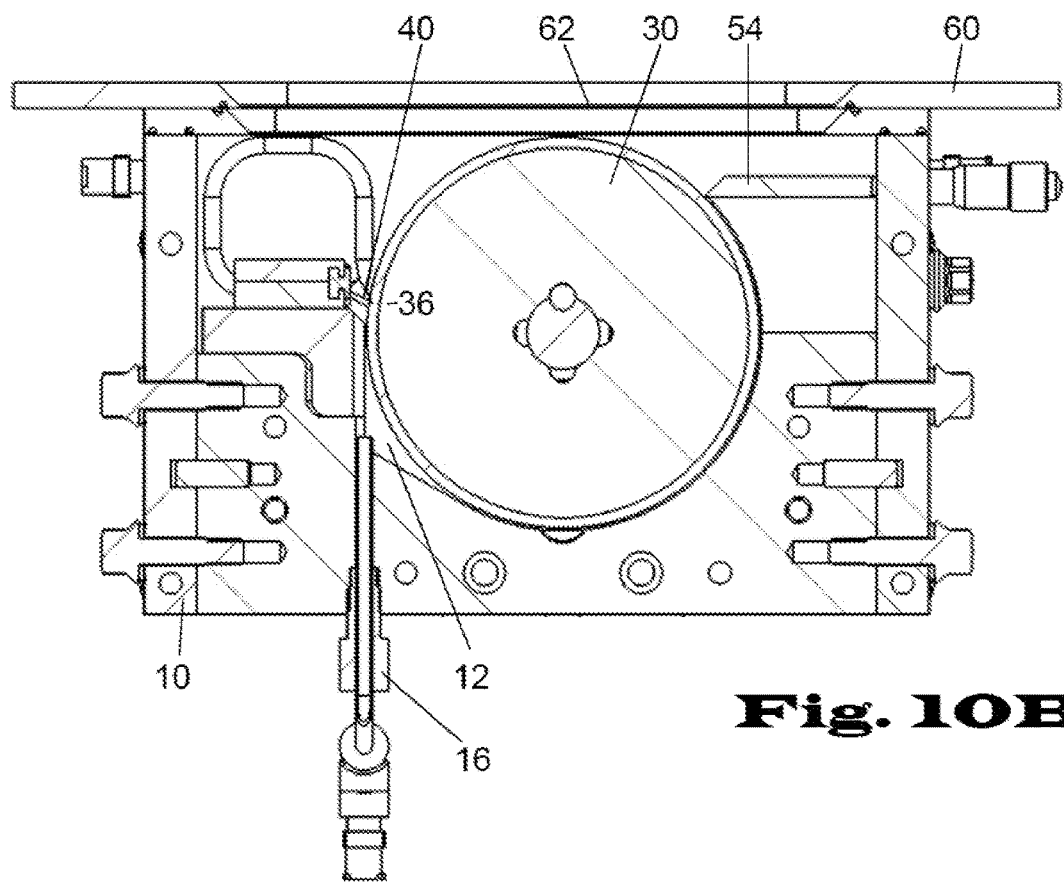

FIGS. 10A and 10B show schematic sectional views of the embodiment of FIG. 9. The sectional plane of FIG. 10A is shown as line "A" in FIG. 9. The sectional plane of FIG. 10B is shown as line "B" in FIG. 9. The reference numbers apply accordingly. The fluid inlet 14 is located on the underside of the tub 12. The outlet 18 projects into the groove formed between the roller 30 and the wiper lip 40. The height of the overflow tube 16 can be varied to determine the fluid level in the tub 12.

The invention claimed is:

1. A cassette for generating a continuous fluid film from supplied biological fluid, suitable for irradiating a generated fluid film and continuously inactivating pathogens in a biological fluid in an arrangement for continuous, dose-controlled irradiation, the cassette comprising:
    a module housing including:
        a tub for holding the biological fluid,
        an inlet channel for supplying the biological fluid to the tub,
        an overflow channel for discharging excess fluid from the tub to fix a fluid level in the tub,
        a cylindrical roller which dips into the tub and fluid and is rotatable within the tub, the cylindrical roller having magnetic elements,
        a wiper lip on a downward-rotating side of the cylindrical roller, the wiper lip in intimate contact with a roller surface of the cylindrical roller to wipe off the generated fluid film formed upon rotation of the cylindrical roller on the roller surface, and
        an outlet channel for receiving and discharging fluid wiped off by the wiper lip;
    a housing cover for closing the module housing, the housing cover having a gas-tight and fluid-tight metal window which is permeable for beta radiation;
    a mechanical or electromechanical drive unit arranged outside of the module housing; and
    a coupling magnetically coupling the mechanical or electromechanical drive unit to the cylindrical roller by way of the magnetic element, the coupling being configured to drive rotation of the cylindrical roller via the mechanical or electromechanical drive unit,
    wherein the cassette is sterilizable and interchangeable for repeated use in the arrangement for continuous, dose-controlled irradiation, and
    wherein the outlet channel is designed as at least one tube projecting into a groove formed between the wiper lip and the downward-rotating side of the cylindrical roller.

2. The cassette according to claim 1, wherein the module housing further comprises:
    a gap-forming element on an upward-rotating side of the cylindrical roller, for forming and homogenizing the generated fluid film on the roller surface, wherein the gap-forming element on the upward-rotating side of the cylindrical roller is spaced from the roller surface in such a manner that it forms a capillary gap, wherein the capillary gap extends to above the fluid level.

3. The cassette according to claim 2, wherein the gap-forming element is positionable at a variable distance from the roller surface, or is exchangeable, to regulate a thickness of the generated fluid film formed thereon.

4. The cassette according to claim 1, which does not contain a gap-forming element.

5. The cassette according to claim 1, wherein the wiper lip on the downward-rotating side of the cylindrical roller is oriented counter to a downward-rotating direction of the cylindrical roller.

6. The cassette according claim 1, wherein the wiper lip on the downward-rotating side of the cylindrical roller is oriented in a downward-rotating direction of the cylindrical roller.

7. The cassette according to claim 1, in combination with an arrangement for the continuous, dose-controlled irradiation of biological fluid for continuous inactivation of pathogens in the biological fluid, comprising:
    a source for beta radiation,
    wherein the cassette is directly coupled to the source for beta radiation.

8. The cassette in combination with the arrangement according to claim 7, further comprising at least one pump for the continuous, active transport of the fluid through the module housing.

9. The cassette in combination with the arrangement according to claim 7, further comprising a mechanical or electromagnetic drive unit for driving a rotation of the cylindrical roller in the module.

10. A method for inactivating pathogens in a biological fluid with the cassette according to claim 1, the method comprising the steps of:
    a) supplying the biological fluid potentially containing active pathogens to the cassette,
    b) rotating the cylindrical roller in the module housing of the cassette such that a continuous fluid film of the biological fluid, of predeterminable thickness, is formed on the roller surface,
    c) irradiating the generated fluid film on the roller surface with ionizing beta radiation in a dose which causes inactivation of the pathogens of the biological fluid, and
    d) collecting the irradiated fluid with inactive pathogens from the roller surface.

* * * * *